United States Patent [19]

Hylton et al.

[11] 4,098,791
[45] Jul. 4, 1978

[54] PROCESS FOR PREPARING 3-(CYANIMINO)-3-AMINO-PROPIONITRILES

[75] Inventors: Thomas A. Hylton, Kalamazoo; Muniraj D. Pillai, Portage, both of Mich.

[73] Assignee: The Upjohn Company, Kalamazoo, Mich.

[21] Appl. No.: 820,161

[22] Filed: Jul. 29, 1977

[51] Int. Cl.$^2$ .................. C07D 295/14; C07D 211/14
[52] U.S. Cl. ........................ 260/293.87; 260/239 A; 260/239 B; 260/326.62; 260/465 E; 260/465.5 R; 544/59; 544/163; 544/323; 544/402; 544/398; 544/295
[58] Field of Search ............... 260/465.5 R, 293.87, 260/239 A, 239 B, 268 CN, 465 E, 326.62; 544/59, 163

[56] References Cited
U.S. PATENT DOCUMENTS 3,910,928 10/1975 McCall et al. .................. 260/293.51
3,948,915 4/1976 Hirayama et al. ............ 260/256.4 C
4,032,559 6/1977 McCall et al. ................. 260/293.87

OTHER PUBLICATIONS
Allenstein, E. et al., Chem. Ber., 100, 2604–2615, (1967); 101, 1232–1243, (1968).
Chemical Abstracts, 78:158999c, (1973), [German Offen. 2,246,376, 3/29/73].

Primary Examiner—Henry R. Jiles
Assistant Examiner—Richard A. Schwartz
Attorney, Agent, or Firm—Hans L. Berneis

[57] ABSTRACT

An improved multistep process for the production of intermediates for hypotensive compounds, which intermediates are of the formula V:

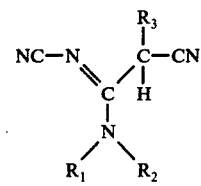

wherein $R_1$ and $R_2$ are lower alkyl of 1 to 4 carbon atoms, inclusive, alkenyl of 3 or 4 carbon atoms, cycloalkyl from 3 to 7 carbon atoms, phenylalkyl in which the alkyl group is defined as above, or the group

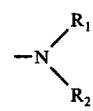

is a heterocyclic moiety of 4 to 8 ring members, e.g., azetidinyl, piperidino, pyrrolidinyl, hexahydroazepinyl, or heptamethyleneimino, each of which can be substituted by one or two methyl groups, N-alkylpiperazino, wherein alkyl is defined as above, morpholino, or thiomorpholino, and wherein $R_3$ is hydrogen or alkyl of 1 to 4 carbon atoms, inclusive, starts with the corresponding secondary amine I

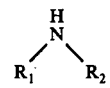

wherein $R_1$ and $R_2$ have the significance of above.

19 Claims, No Drawings

PROCESS FOR PREPARING 3-(CYANIMINO)-3-AMINO-PROPIONITRILES su

BRIEF SUMMARY OF THE INVENTION

This invention is concerned with a new, improved process for the production of 2,N-dicyanoacetamidines which are the primary intermediates for anti-hypertensive 2,4-diamino-6-aminopyrimidine-3-oxides.

This process can be illustratively represented as follows:

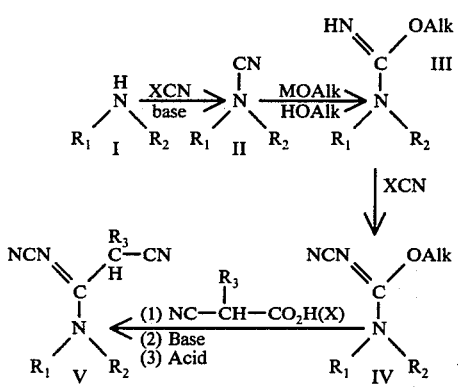

wherein $R_1$ and $R_2$ are alkyl of 1 to 4 carbon atoms, inclusive, alkenyl of 3 to 4 carbon atoms inclusive, cycloalkyl from 3 to 7 carbon atoms, inclusive, phenylalkyl in which the alkyl group is defined as above, or the group

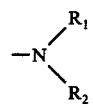

is a heterocyclic moiety of 4 to 8 ring members, e.g., azetidinyl, pyrrolidinyl, piperidino, hexahydroazepinyl, or heptamethyleneimino, each of which can be substituted by 1 to 2 methyl groups, or 4-morpholino, 4-thiomorpholino, or N-alkylpiperazino, in which alkyl is defined as above; wherein $R_3$ is hydrogen or alkyl defined as above, wherein X is chlorine, bromine or iodine. M is a metal ion selected from the group consisting of lithium, sodium, potassium, magnesium, calcium or aluminum, and Alk is alkyl of 1 to 4 carbon atoms, inclusive.

From compounds of formula V, the final desired compounds VI are prepared by the single step:

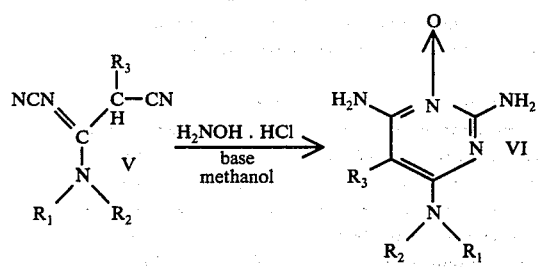

See U.S. Pat. No. 3,910,928.

FIELD OF THE INVENTION

The principal compound in this field is the compound in which

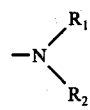

is piperidino; thus the intermediate has the formula Va (below), and the final product has the formula VIa (below), produced by the process

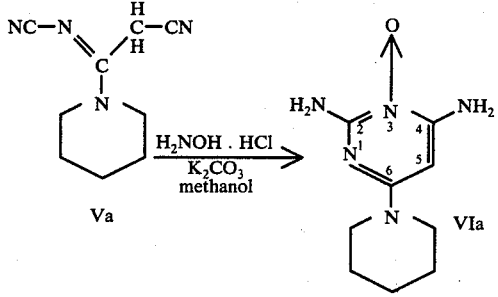

Prior to the present invention, compound Va has been produced by the following process:

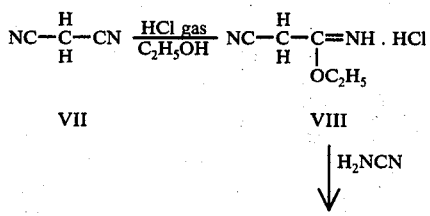

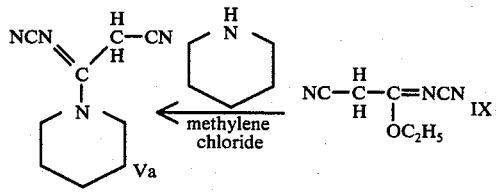

In the present new process the intermediate Va is produced by the following specific synthesis:

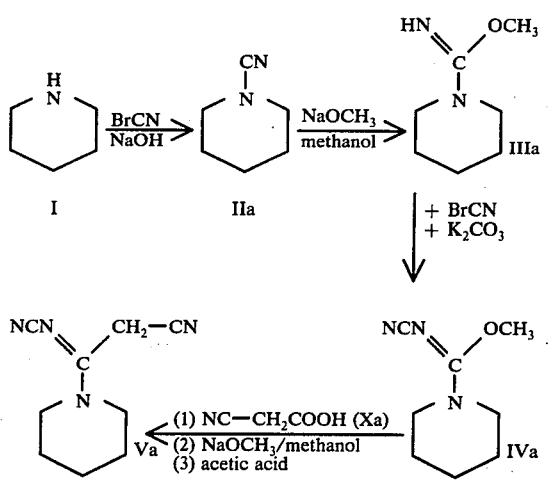

The advantages in this process are:

(1) the cost of the new process is less, since the price of cyanoacetic acid is only about one-third of that of malononitrile;

(2) the new process provides 20–25% relative yield increase with a lower cost.

In the new four-step synthesis of this invention, the step IV to V is similar to the reaction described in J. Chem. Soc. Chemical Communication, page 350, 1974, by Kristinsson. However, Kristinsson used cyanoacetic acid ethyl ester rather than the free acid, and as a result the carbethoxy group was incorporated into a new ring (a uracil ring). Thus, the process of Kristinsson cannot be used in this synthesis to give compounds of structure V, and therefore the last step is novel.

DETAILED DESCRIPTION

The preferred process of this invention is that in which the starting compounds are heterocyclic secondary amines, such as pyrrolidine, piperidine, morpholine, thiomorpholine, hexahydroazepine, heptamethyleneimine or N-alkylpiperazine in which alkyl is of 1 to 4 carbon atoms, inclusive. Most preferred of these starting compounds is piperidine, of which the process (with starting compound Ia) has been described above. The process with starting compound Ia provides the compound Va. Compound Va is the last intermediate used to make compound VIa:

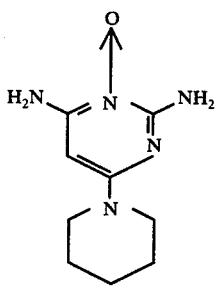

Compound VIa, under the generic name, minoxidil, is one of the more effective drugs in the treatment of hypertension, and works particularly well in the treatment of patients having toxic hypertension, often intractable by other drugs, and the patients are therefore in acute danger of life. Minoxidil is still a clinical experimental drug.

Other compounds of formula VI also have been found to be anti-hypertensives and are useful for the treatment of hypertensive patients.

U.S. Pat. No. 3,461,461 provides the details of how to use the compounds of formula VI in oral and parenteral formulations and the dosages and modes of administration.

The new process for the final intermediates of formula V, herein claimed, is useful to lower the price of the final medicament of formula VI.

In carrying out the process of the invention, a selected secondary amine of formula I is reacted in solution with cyanogen halide and a base. Solvents used in this reaction include water, ether and non-polar organic solvents, such as diethyl or dipropyl ether, methylethyl ether, tetrahydrofuran, ethyl acetate, acetone and hydrocarbons, e.g., pentane, hexane, toluene and the like. The reaction temperature is preferably kept low, between about 0° and 15° C. when water is solvent, and can be lower for the organic solvents. A two-phase system, water-organic solvent, is preferred. As bases, sodium or potassium hydroxide or carbonate are preferred, usually in aqueous solution. In the preferred embodiment of this invention a solution of the secondary amine is cooled to 0° to 10° C. and cyanogen halide is slowly added, in small portions, using an excess of 10% to 25%. Larger excess of this reagent is operative, but is not necessary or desirable. The base, aqueous sodium or potassium hydroxide is preferred, is added slowly and the temperature is kept at the low level of 0° to 10° C. After stirring for ½ to 2 hours, the product II, the carbonitrile of the amine, is isolated and purified by conventional procedures, such as extraction, washing, chromatography, crystallization, distillation and the like. Cyanogen halide used in this process is available commercially or can be made by standard methods, e.g., using sodium cyanide and a halogen source.

Compound II is treated with a metal alkoxide of which the alkyl group of the alkoxide is of 1 to 4 carbon atoms, inclusive, and the metal is lithium, sodium, potassium, magnesium or aluminum, in a lower alkanol solution of 1 to 4 carbon atoms, inclusive, to give compound III. Sodium or potassium methoxide or ethoxide is preferred. In the preferred embodiment of the invention the N-carbonitrile of the amine (II) in methanol is reacted at 10° to 50° C. preferably at room temperature (20° to 30° C.) with the methoxide. Higher or lower temperatures can be selected and are operative in this reaction. The reaction time is from 2 to 48 hours. At the termination of the reaction the resultant compound, a methyl 1-aminocarboximidate (III), is isolated and purified by conventional means, e.g., extraction, evaporation, crystallization, distillation or the like.

Compound III in solution is treated with a cyanogen halide and thereto is added a base to produce compound IV. As solvent, ethers, e.g., methylethyl, diethyl, ethylpropyl ether or tetrahydrofuran, or hydrocarbons, e.g., hexane or toluene, or mixtures thereof, or the like may be used. As base sodium or potassium carbonate or bicarbonate is utilized. In the preferred embodiment of this invention to a solution of compound III in an ether is added cyanogen bromide followed by anhydrous sodium or potassium carbonate. The reaction is carried out between 0° C. and the boiling temperature of the solvent, with room temperature preferred. The reaction time is between 2 to 48 hours. After the reaction is terminated, the product IV, a methyl N'-cyano-1-carboximidate, is isolated and purified by conventional means, e.g., filtration, evaporation, extraction, chromatography, crystallization or the like.

Compound IV is converted to compound V, a 2,N-dicyanoacetamidine, by treating a solution of IV with a solution of a cyanoacetic acid of formula X, and a base. Preferred bases are sodium or potassium alkoxides. As solvents alcohols, e.g., methanol, ethanol and the like, ethers, e.g., tetrahydrofuran, diethylether, hydrocarbons, e.g., benzene, toluene and the like, dimethylformamide, or mixtures thereof, or the like can be used. The solution of the cyanoacetic acid VII and base is mixed with a solution of compound IV in one of the beforementioned solvents. The mixture is stirred from 1 to 48 hours at temperatures between 0° and 50° C. with room temperature (20° to 30° C.) preferred.

After the reaction is terminated, the solution is acidified, preferably with acetic acid, evaporated and extracted. The product is isolated from the extracts and purified in conventional manners, e.g., by extraction, crystallization, chromatography, distillation or the like.

Starting cyanoacetic acids if not commercially available can be synthesized by the method cited by R. B. Wagner et al. in "Synthetic Organic Chemistry", John Wiley (1965) p. 593.

The following examples are illustrative of the products and processes of the present invention but are not construed to be limiting.

EXAMPLE 1

1-Piperidinecarbonitrile

To a solution of 70 g. (0.82 mole) of piperidine in 200 ml. of water, kept cold in an ice bath, are added simultaneously over a period of one hour, in small portions, 100 g. (0.94 mole) of cyanogen bromide and (in a separate addition funnel) a solution of 37 g. (0.93 mole) of sodium hydroxide in 200 ml. of water. The addition of cyanogen bromide is very exothermic. An oily layer begins to form after about half of the reagents have been added.

The mixture is stirred at 0° C. for 1 hour, then the layers are separated and the aqueous layer is extracted with three portions of benzene. The combined organic solution is washed with water and saturated sodium chloride solution and evaporated. The oily residue is distilled under high vacuum to give 85.8 g. (94.7%) of 1-piperidinecarbonitrile as a colorless oil of boiling point 45° C./0.1 mm.

EXAMPLE 2

Methyl 1-piperidinecarboximidate

A solution of 45.2 g. (0.41 mole) of 1-piperidinecarbonitrile and 11 g. (0.05 mole) of a 25% solution of sodium methoxide in methanol in 200 ml. of methanol is stirred at room temperature under a nitrogen atmosphere for 18 hours. The solvent is evaporated and the residue is taken up in ether. The ether solution is filtered through a small pad of Celite and evaporated to constant weight to give 57.8 g. (99%) of a colorless oil.

EXAMPLE 3

Methyl N-cyano-1-piperidinecarboximidate

To a stirred solution of 1.42 g. (10 millimoles) of freshly prepared methyl 1-piperidinecarboximidate in 25 ml. of anhydrous ether, under a dry nitrogen atmosphere, is added 1.1 g. (10 millimoles) of cyanogen bromide, followed by 1.38 g. (10 millimoles) of anhydrous potassium carbonate. After 17 hours the slurry thus obtained is filtered and the filtrate evaporated to constant weight to give 1.39 g. (82%) of methyl N-cyano-1-piperidinecarboximidate as a colorless oil; ir (film): 4.52$\mu$ (—CN) and 6.2$\mu$ (—C≡N); nmr (CDCl$_3$): 1.64$\delta$ (6H, broad) and 3.66$\delta$ (4H, broad) from the piperidine ring, and 3.92$\delta$ (3H, sing., —OCH$_3$).

EXAMPLE 4

2,-N-Dicyano-N',N'-pentamethyleneacetamidine

A solution of 0.710 g. (8.3 millimoles) of cyanoacetic acid and 4.0 g. (18.5 millimoles) of 25% sodium methoxide in methanol solution in 10 ml. of tetrahydrofuran is stirred at 0° C. under a nitrogen atmosphere for 2 hours. A solution of 1.35 g. (8.1 millimoles) of methyl N-cyano-1-piperidinecarboximidate in 20 ml. of tetrahydrofuran is added, and the mixture is allowed to stir two hours at room temperature. After one day, 2.0 g. (9.3 millimoles) of 25% sodium methoxide in methanol solution is added, and within 4 hours the mixture turns yellow-brown in color.

The following day (total of two days) the mixture is quenched with 16 ml. of a 1:1 mixture of acetic acid and methanol and stirred at room temperature for 1.5 days (the solution becomes clear after several hours). The mixture is concentrated and the residue is partitioned between methylene chloride and water. The aqueous part is extracted twice with methylene chloride, and the combined organic phases are washed with water, dried and evaporated to constant weight to give 0.99 g. (70%) of 2,N-dicyano-N',N'-pentamethyleneacetamidine as an oil which rapidly crystallizes; ir (chloroform): 4.52$\mu$ (—CN, only one band observed) and 6.25$\mu$ (—C≡N—); nmr (CDCl$_3$): 1.72$\delta$ (broad singlet) and 3.68$\delta$ (very broad peak) are the piperidine ring protons, and 3.90$\delta$ (sharp singlet).

EXAMPLE 5

Diethylamine-N-carbonitrile

In the manner given in Example 1, diethylamine is treated with cyanogen bromide and aqueous sodium hydroxide to give diethylamine-N-carbonitrile.

EXAMPLE 6

Methyl 1-Diethylaminecarboximidate

In the manner given in Example 2, diethylamine-N-carbonitrile is treated with sodium methoxide in methanol to give methyl diethylaminecarboximidate.

EXAMPLE 7

Methyl N-cyano-1-diethylaminecarboximidate

In the manner given in Example 3, methyl diethylamine-N-carboximidate is reacted with cyanogen bromide and then with sodium carbonate to give methyl N-cyano-1-diethylaminecarboximidate.

EXAMPLE 8

2,N-Dicyano-N',N'-diethylacetamidine

In the manner given in Example 4, to a solution of cyano acetic acid and sodium methoxide in methanol is added a solution of methyl N-cyano-1-diethylaminecarboximidate in tetrahydrofuran to give 2,N-dicyano-N',N'-diethylacetamidine.

EXAMPLE 9

Dipropylamine-N-carbonitrile

In the manner given in Example 1, dipropylamine is treated with cyanogen bromide and aqueous sodium hydroxide to give dipropylamine-N-carbonitrile.

EXAMPLE 10

Methyl 1-dipropylaminecarboximidate

In the manner given in Example 2, dipropylamine-N-carbonitrile is treated with sodium methoxide in methanol to give methyl 1-dipropylaminecarboximidate.

EXAMPLE 11

Methyl N-cyano-1-dipropylaminecarboximidate

In the manner given in Example 3, methyl 1-dipropylaminecarboximidate is reacted with cyanogen bromide and then with potassium carbonate to give methyl N-cyano-1-dipropylaminecarboximidate.

EXAMPLE 12

2,N-Dicyano-N',N'-dipropylacetamidine

In the manner given in Example 4, to a solution of cyanoacetic acid and sodium methoxide in methanol is added a solution of methyl N-cyano-2-dipropylaminecarboximidate to give 2,N-dicyano-N',N'-dipropylacetamidine.

EXAMPLE 13

Dibutylamine-N-carbonitrile

In the manner given in Example 1, dibutylamine is treated with cyanogen chloride and aqueous sodium hydroxide to give dibutylamine-N-carbonitrile.

EXAMPLE 14

Ethyl 1-dibutylaminecarboximidate

In the manner given in Example 2, dibutylamine-N-carbonitrile is treated with potassium ethoxide in ethanol to give ethyl 1-dibutylaminecarboximidate.

EXAMPLE 15

Ethyl N-cyano-2-dibutylaminecarboximidate

In the manner given in Example 3, ethyl 1-dibutylaminecarboximidate is reacted with cyanogen chloride and then with sodium carbonate to give ethyl N-cyano-1-dibutylaminecarboximidate.

EXAMPLE 16

2,N-Dicyano-N',N'-dibutylacetamidine

In the manner given in Example 4, to a solution of cyanoacetic acid and sodium methoxide in methanol is added a solution of ethyl N-cyano-1-dibutylaminecarboximidate in diethyl ether to give 2,N-dicyano-N',N'-dibutylacetamidine.

EXAMPLE 17

4-Methyl-1-piperidinecarbonitrile

In the manner given in Example 1, 4-methylpiperidine is treated with cyanogen bromide and aqueous sodium sodium hydroxide to give 4-methyl-1-piperidinecarbonitrile.

EXAMPLE 18

Methyl 4-methyl-1-piperidinecarboximidate

In the manner given in Example 2, methyl 4-methyl-1-piperidinecarbonitrile is treated with sodium methoxide in methanol to give methyl 4-methyl-1-piperidinecarboximidate.

EXAMPLE 19

Methyl N-cyano-4-methyl-1-piperidinecarboximidate

In the manner given in Example 3, methyl 4-methyl-1-piperidinecarboximidate is reacted with cyanogen bromide and then with potassium carbonate to give methyl N-cyano-4-methyl-1-piperidinecarboximidate.

EXAMPLE 20

2,N-dicyano-1-(3-methylpentamethylene)acetamidine

In the manner given in Example 4, to a solution of cyanoacetic acid and sodium methoxide in methanol is added a solution of methyl N-cyano-4-methyl-1-piperidinecarboximidate in tetrahydrofuran to give 2,N-dicyano-1-(3-methylpentamethylene)acetamidine.

EXAMPLE 21

1-Pyrrolidinecarbonitrile

In the manner given in Example 1, pyrrolidine is treated with cyanogen bromide and aqueous sodium hydroxide to give 1-pyrrolidinecarbonitrile.

EXAMPLE 22

Methyl 1-pyrrolidinecarboximidate

In the manner given in Example 2, 1-pyrrolidinecarbonitrile is treated with sodium methoxide in methanol to give methyl 1-pyrrolidinecarboximidate.

EXAMPLE 23

Methyl N-cyano-1-pyrrolidinecarboximidate

In the manner given in Example 3, methyl 1-pyrrolidinecarboximidate is reacted with cyanogen bromide and then with potassium carbonate to give methyl N-cyano-1-pyrrolidinecarboximidate.

EXAMPLE 24

2-Methyl-2,N-dicyano-N',N'-tetramethyleneacetamidine

In the manner given in Example 4, to a solution of 2-cyanopropionic acid and sodium methoxide in methanol is added a solution of methyl N-cyano-1-pyrrolidinecarboximidate in dioxane to give 2-methyl-2,N-dicyano-N',N'-tetramethyleneacetamidine.

EXAMPLE 25

1-Hexahydroazepinecarbonitrile

In the manner given in Example 1, hexahydroazepine is treated with cyanogen bromide and aqueous sodium hydroxide to give 1-hexahydroazepinecarbonitrile.

EXAMPLE 26

Methyl 1-hexahydroazepinecarboximidate

In the manner given in Example 2, 1-hexahydroazepinecarbonitrile is treated with sodium methoxide in methanol to give methyl 1-hexahydrazepinecarboximidate.

EXAMPLE 27

Methyl N-cyano-1-hexahydroazepinecarboximidate

In the manner given in Example 3, methyl 1-hexahydroazepinecarboximidate is reacted with cyanogen bromide and then with potassium carbonate to give methyl N-cyano-1-hexahydroazepinecarboximidate.

EXAMPLE 28

2,N-Dicyano-N',N'-hexamethyleneacetamidine

In the manner given in Example 4, to a solution of cyanoacetic acid and sodium methoxide in methanol is added a solution of methyl N-cyano-1-hexahydroazepinecarboximidate in tetrahydrofuran to give 2,N-dicyano-N',N'-hexamethyleneacetamidine.

EXAMPLE 29

4-Morpholinecarbonitrile

In the manner given in Example 1, morpholine is treated with cyanogen bromide and aqueous sodium hydroxide to give 4-morpholinecarbonitrile.

EXAMPLE 30

Methyl 4-morpholinecarboximidate

In the manner given in Example 2, 4-morpholinecarbonitrile is treated with sodium methoxide in methanol to give methyl 4-morpholinecarboximidate.

EXAMPLE 31

Methyl N-cyano-4-morpholinecarboximidate

In the manner given in Example 3, methyl 4-morpholinecarboximidate is reacted with cyanogen bromide and then with potassium carbonate to give methyl N-cyano-4-morpholinecarboximidate.

EXAMPLE 32

2,N-Dicyano-N',N'-(2,2'-oxydiethyl)acetamidine

In the manner given in Example 4, to a solution of cyanoacetic acid and sodium methoxide in methanol is added a solution of methyl N-cyano-4-morpholinecarboximidate in diethyl ether to give 2,N-dicyano-N',N'-(2,2'-oxydiethyl)-acetamidine.

EXAMPLE 33

4-Methyl-1-piperazinecarbonitrile

In the manner given in Example 1, N-methylpiperazine is treated with cyanogen bromide and aqueous sodium hydroxide to give 4-methyl-1-piperazinecarbonitrile.

EXAMPLE 34

Methyl 4-methyl-1-piperazinecarboximidate

In the manner given in Example 2, 4-methyl-1-piperazinecarbonitrile is treated with sodium methoxide in methanol to give methyl 4-methyl-1-piperazinecarboximidate.

EXAMPLE 35

Methyl N-cyano-4-methyl-1-piperazinecarboximidate

In the manner given in Example 3, methyl 4-methyl-1-piperazinecarboximidate is reacted with cyanogen bromide and then with potassium carbonate to give methyl N-cyano-4-methyl-1-piperazinecarboximidate.

EXAMPLE 36

2,N-dicyano-N',N'-(2,2'-methylaminodiethyl)-acetamidine

In the manner given in Example 4, to a solution of cyanoacetic acid and sodium methoxide in methanol is added a solution of methyl N-cyano-4-methyl-1-piperazinecarboximidate in tetrahydrofuran to give 2,N-dicyano-N',N'-(2,2'-methylaminodiethyl)acetamidine.

EXAMPLE 37

N-(N-benzyl-N-methylamine)carbonitrile

In the manner given in Example 1, benzylmethylamine is treated with cyanogen bromide and aqueous sodium hydroxide to give N-(N-benzyl-N-methylamine)-carbonitrile.

EXAMPLE 38

Methyl 1-(N-benzyl-N-methylamine)carboximidate

In the manner given in Example 2, N-(N-benzyl-N-methylamine)carbonitrile is treated with sodium methoxide in methanol to give methyl 1-(N-benzyl-N-methylamine)-carboximidate.

EXAMPLE 39

Methyl N-cyano-1-(N-benzyl-N-methylamine)carboximidate

In the manner given in Example 3, methyl 1-(N-benzyl-N-methylamine)carboximidate is reacted with cyanogen bromide and then with potassium carbonate to give methyl N-cyano-1-(N-benzyl-N-methylamine)carboximidate.

EXAMPLE 40

2,N-Dicyano-N'-benzyl-N'-methylacetamidine

In the manner given in Example 4, to a solution of cyanoacetic acid and sodium propoxide in propanol is added a solution of methyl N-cyano-1-(N-benzyl-N-methylamine)carboximidate in tetrahydrofuran, to give 2,N-dicyano-N'-benzyl-N'-methylacetamidine.

EXAMPLE 41

1-Di(cyclopropyl)aminecarbonitrile

In the manner given in Example 1, di(cyclopropyl)amine is treated with cyanogen bromide and aqueous sodium hydroxide to give 1-di(cyclopropyl)aminecarbonitrile.

EXAMPLE 42

Methyl 1-di(cyclopropyl)aminecarboximidate

In the manner given in Example 2, 1-di(cyclopropyl)aminecarbonitrile is treated with sodium methoxide in methanol to give methyl 1-di(cyclopropyl)aminecarboximidate.

EXAMPLE 43

Methyl N-cyano-1-di(cyclopropyl)aminecarboximidate

In the manner given in Example 3, methyl 1-di(cyclopropyl)aminecarboximidate is treated with cyanogen bromide and then with potassium carbonate to give methyl N-cyano-1-di(cyclopropyl)aminecarboximidate.

EXAMPLE 44

2-N-Dicyano-N',N'-di(cyclopropyl)acetamidine

In the manner given in Example 4, to a solution of cyanoacetic acid and sodium methoxide in methanol is added a solution of methyl N-cyano-1-di(cyclopropyl)aminecarboximidate in tetrahydrofuran to give 2,N-dicyano-N',N'-di(cyclopropyl)acetamidine.

EXAMPLE 45

1-Diallylaminecarbonitrile

In the manner given in Example 1, diallylamine is treated with cyanogen bromide and aqueous sodium hydroxide to give 1-diallylaminecarbonitrile.

EXAMPLE 46

Methyl 1-diallylaminecarboximidate

In the manner given in Example 2, 1-diallylaminecarbonitrile is treated with sodium methoxide in methanol to give methyl 1-diallylaminecarboximidate.

EXAMPLE 47

Methyl N-cyano-1-diallylaminecarboximidate

In the manner given in Example 3, methyl 1-diallylaminecarboximidate is reacted with cyanogen bromide and then with sodium carbonate to give methyl N-cyano-1-diallylaminecarboximidate.

EXAMPLE 48

2,N-Dicyano-N',N'-diallylacetamidine

In the manner given in Example 4, to a solution of cyanoacetic acid and sodium methoxide in methanol is added a solution of methyl N-cyano-1-diallylaminecarboximidate in tetrahydrofuran to give 2,N-dicyano-N',N'-diallylacetamidine.

EXAMPLE 49

1-Di(cyclohexyl)aminecarbonitrile

In the manner given in Example 1, di(cyclohexyl)amine is treated with cyanogen bromide and aqueous sodium hydroxide to give 1-di(cyclohexyl)aminecarbonitrile.

EXAMPLE 50

Methyl 1-di(cyclohexyl)aminecarboximidate

In the manner given in Example 2, di(cyclohexyl)aminecarbonitrile is treated with sodium methoxide in methanol to give methyl-1-(dicyclohexyl)aminecarboximidate.

EXAMPLE 51

Methyl N-cyano-1-di(cyclohexyl)aminecarboximidate

In the manner given in Example 3, methyl 1-di(cyclohexyl)aminecarboximidate is reacted with cyanogen chloride and then with potassium carbonate to give methyl N-cyano-1-di(cyclohexyl)aminecarboximidate.

EXAMPLE 52

2,N-Dicyano-N',N'-di(cyclohexyl)acetamidine

In the manner given in Example 4, to a solution of cyano acetic acid and sodium methoxide in methanol is added a solution of methyl N-cyano-1-di(cyclohexyl)aminecarboximidate in tetrahydrofuran to give 2,N-dicyano-N',N'-di(cyclohexyl)acetamidine.

In the manner given in the prior examples other 2,N-dicyanoacetamidines of formula V can be obtained. Representative compounds of formula V thus obtained include, e.g.,:

2,N-dicyano-N'-methyl-N'-ethylacetamidine,
2,N-dicyano-N'-methyl-N'-propylacetamidine,
2,N-dicyano-N'-methyl-N'-butylacetamidine,
2,N-dicyano-N'-ethyl-N'-butylacetamidine,
2,N-dicyano-N'-ethyl-N'-propylacetamidine,
2,N-dicyano-N'-cyclopropyl-N'-methylacetamidine,
2,N-dicyano-N'-cyclopropyl-N'-butylacetamidine,
2,N-dicyano-N'-propyl-N'-(3-butenyl)acetamidine,
2,N-dicyano-N',N'-trimethyleneacetamidine,
2,N-dicyano-N',N'-heptamethyleneacetamidine,
2,N-dicyano-N',N'-(2,2'-ethylaminodiethyl)acetamidine,
2,N-dicyano-N',N'-(2,2'-thiodiethyl)acetamidine,
2,N-dicyano-N'-cyclohexyl-N'-methylacetamidine,
2-methyl-2,N-dicyano-N'-ethyl-N'-butylacetamidine,
2-methyl-2,N-dicyano-N'-methyl N'-phenethylacetamidine, and the like.

We claim:

1. A process for the production of a compound of formula V:

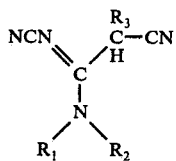

wherein $R_1$ and $R_2$ are alkyl of 1 to 4 carbon atoms, inclusive, alkenyl of 3 or 4 carbon atoms, inclusive, cycloalkyl from 3 to 7 carbon atoms, inclusive, phenylalkyl in which the alkyl group is defined as above, or the group

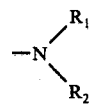

is 1-azetidinyl, pyrrolidino, piperidino, hexahydroazepino, heptamethyleneimino, each of which can be substituted with 1 or 2 methyl groups, or 4-morpholinyl, 4-thiomorpholinyl, or N-alkylpiperazino, in which the alkyl group is defined as above; wherein $R_3$ is hydrogen or alkyl as defined above, which comprises:

(1) treating a compound of the formula I

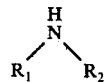

wherein $R_1$ and $R_2$ or

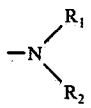

are defined as above, with a cyanogen halide in which the halogen is chlorine, bromine or iodine, in the presence of a base to obtain the compound of formula II:

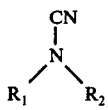

wherein R₁ and R₂ are defined as above;

(2) treated compound II with a metal alkoxide wherein the alkyl group Alk of the alkoxy moiety is of 1 to 4 carbon atoms, inclusive, and the metal is lithium, sodium, potassium, magnesium, or aluminum, in an alkanol of 1 to 4 carbon atoms, inclusive, to obtain compound III:

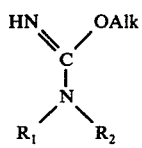

wherein R₁, R₂ and Alk are defined as above;

(3) treating compound III with cyanogen halide and a base to obtain compound IV:

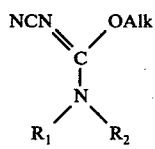

wherein halogen, R₁, R₂ and Alk are defined as above; and (4) treating compound IV with a cyanoacetic acid of the formula:

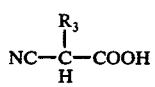

wherein R₃ is hydrogen or alkyl as defined above, and a base followed by acid treatment to obtain the compound of formula V above.

2. The process of claim 1 wherein the compound of formula I is pyrrolidine, piperidine, morpholine, thiomorpholine, hexahydroazepine, heptamethyleneimine, each of which can be substituted with one or two methyl groups, or N-alkylpiperazine in which the alkyl group is from 1 to 4 carbon atoms, inclusive.

3. The process of claim 1 wherein the compound of formula I is a dialkylamine in which alkyl is of 1 to 4 carbon atoms, inclusive.

4. The process of claim 1 wherein compound X is cyanoacetic acid.

5. A process for the production of a 2,N-dicyano-N',N'-pentamethyleneacetamidine of the formula XIII:

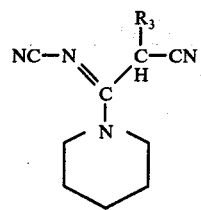

wherein R₃ is hydrogen or alkyl of 1 to 4 carbon atoms inclusive, which comprises:

(1) treating piperidine:

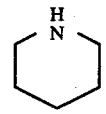

with cyanogen halide and a base at about 0° to 15° C. to give compound IIa:

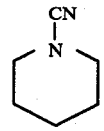

(2) treating IIa with a sodium or potassium alkoxide in which the alkyl group Alk of the alkoxide moiety is of 1 to 4 carbon atoms, inclusive, to give compound XI

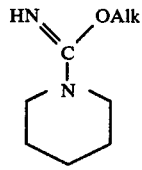

(3) treating compound XI with a cyanogen halide wherein the halogen is chlorine, bromine or iodine and a base to obtain compound XII:

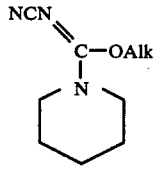

wherein Alk is alkyl defined as above; and (4) treating compound XII with a cyanoacetic acid of the formula X

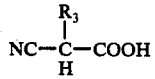

wherein R₃ is as defined above, and with sodium or potassium alkoxide, defined as above, followed by acid treatment to obtain a compound of formula XIII above.

6. A process for the production of 2,N-dicyano-N',N'-pentamethyleneacetamidine of the formula Va:

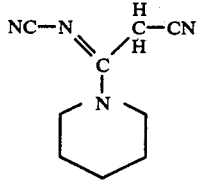

which comprises:
(1) treating piperidine with cyanogen halide and a base at about 0° to 15° C. to give compound IIa:

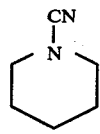

(2) treating IIa with a sodium or potassium alkoxide in which the alkyl group Alk of the alkoxide moiety is of 1 to 4 carbon atoms, inclusive, to give compound XI:

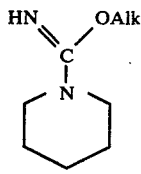

(3) treating compound XI with cyanogen halide and a base to obtain compound XII:

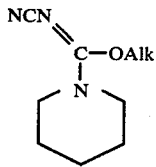

(4) and treating compound XII with cyanoacetic acid and a sodium or potassium alkoxide defined as above followed by acid treatment to obtain the compound of formula Va above.

7. The process of claim 6 wherein the base used in step 1 is sodium or potassium hydroxide.

8. The process of claim 6 wherein the base used in step 3 is anhydrous sodium or potassium carbonate.

9. The process of claim 6 wherein for the acid treatment in step 4, acetic acid is used.

10. The process of claim 6 wherein in step 4 the sodium alkoxide is sodium methoxide.

11. A process for the production of a compound of formula V:

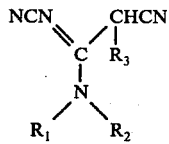

wherein $R_1$ and $R_2$ are alkyl of 1 to 4 carbon atoms, inclusive, alkenyl of 3 or 4 carbon atoms, inclusive, cycloalkyl from 3 to 7 carbon atoms, inclusive, phenylalkyl in which the alkyl group is defined as above, or the group

is 1-azetidinyl, pyrrolidino, piperidino, hexahydroazepino, heptamethyleneimino, each of which can be substituted with 1 or 2 methyl groups, or 4-morpholinyl, 4-thiomorpholinyl, or N-alkylpiperazine, in which the alkyl group is defined as above; wherein $R_3$ is hydrogen or alkyl as defined above, which comprises treating a compound IV:

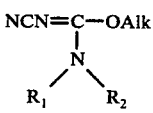

wherein $R_1$ and $R_2$ are defined as above and Alk is an alkyl of 1 to 4 carbon atoms, inclusive, with a compound of formula X

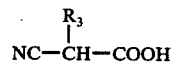

wherein $R_3$ is defined as above, in the presence of a metal alkoxide, wherein the metal is lithium, sodium, potassium, magnesium, or aluminum, and treating the resultant compound with an acid to obtain the compound of formula V.

12. A process according to claim 11 wherein $R_1$ and $R_2$ are alkyl of 1 to 4 carbon atoms, inclusive, or the group

is 1-azetidinyl, pyrrolidino, piperidino, hexahydroazepino, heptamethyleneimino, each of which can be substituted with 1 or 2 methyl groups, 4-morpholinyl, 4-thiomorpholinyl, or N-alkylpiperazino, in which the alkyl group is defined as above.

13. A process according to claim 12 wherein $R_3$ is hydrogen.

14. A process for the production of the compound of formula XIII:

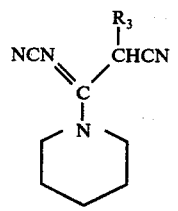

wherein $R_3$ is H or alkyl of 1 to 4 carbon atoms, inclusive, which comprises treating compound XII:

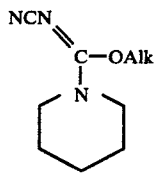

wherein Alk is alkyl of 1 to 4 carbon atoms, inclusive, with a compound of formula X:

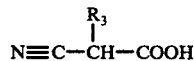

wherein $R_3$ is defined as above, and a metal alkoxide, wherein the metal is lithium, sodium, potassium, magnesium or aluminum, followed by acid treatment to give the compound of formula XIII.

15. The process of claim 14 wherein $R_3$ is hydrogen.

16. The process of claim 15 wherein the acid treatment is carried out with acetic acid.

17. The process of claim 15 wherein the metal alkoxide is sodium or potassium methoxide.

18. A process for the production of 2,N-dicyano-N',N'-pentamethyleneacetamidine which comprises:

treating methyl N-cyano-1-piperidinecarboximidate with cyanoacetic acid and sodium or potassium alkoxide, wherein the alkyl group of the alkoxy moiety is of 1 to 4 carbon atoms, inclusive, followed by acid treatment to obtain 2,N-dicyano-N',N'-pentamethyleneacetamidine.

19. The process of claim 18 wherein the sodium alkoxide is sodium methoxide.

* * * * *